United States Patent
Walti et al.

(10) Patent No.: US 11,554,205 B2
(45) Date of Patent: Jan. 17, 2023

(54) APPLIANCE AND METHOD FOR WOUND THERAPY BY MEANS OF NEGATIVE PRESSURE AND DELIVERY OF A SUBSTANCE

(71) Applicant: MEDELA HOLDING AG, Baar (CH)

(72) Inventors: Martin Walti, Zurich (CH); Tobias Hänggi, Cham (CH)

(73) Assignee: MEDELA HOLDING AG, Baar (CH)

( * ) Notice: Subject to any disclaimer, the term of this patent is extended or adjusted under 35 U.S.C. 154(b) by 162 days.

(21) Appl. No.: 16/473,958

(22) PCT Filed: Jan. 5, 2018

(86) PCT No.: PCT/EP2018/050275
§ 371 (c)(1),
(2) Date: Jun. 26, 2019

(87) PCT Pub. No.: WO2018/130466
PCT Pub. Date: Jul. 19, 2018

(65) Prior Publication Data
US 2019/0365961 A1 Dec. 5, 2019

(30) Foreign Application Priority Data
Jan. 10, 2017 (EP) .................................... 17150814

(51) Int. Cl.
*A61M 3/02* (2006.01)
*A61M 1/00* (2006.01)

(52) U.S. Cl.
CPC .............. *A61M 1/90* (2021.05); *A61M 1/75* (2021.05); *A61M 1/777* (2021.05); *A61M 1/85* (2021.05);
(Continued)

(58) Field of Classification Search
CPC .. A61M 1/0088; A61M 1/006; A61M 1/0037; A61M 1/0084; A61M 3/022;
(Continued)

(56) References Cited

U.S. PATENT DOCUMENTS

2010/0259283 A1 10/2010 Togura
2011/0034861 A1* 2/2011 Schaefer ............... A61M 35/30
604/23

(Continued)

FOREIGN PATENT DOCUMENTS

DE 102013226708 A1 6/2015
EP 0 865 304 B1 7/2001
(Continued)

OTHER PUBLICATIONS

International Search Report for Interntional Application No. PCT/EP2018/050275, dated Apr. 4, 2018.
(Continued)

*Primary Examiner* — Andrew J Mensh
(74) *Attorney, Agent, or Firm* — Marshall, Gerstein & Borun LLP

(57) ABSTRACT

An appliance is provided for negative-pressure therapy of wounds on the human or animal body in which, on the one hand, a substance is delivered to a wound bed (W) and, on the other hand, fluids, in particular an exudate and the delivered substance, are aspirated from the wound bed by negative pressure. The appliance has a suction pump housing, with a suction pump arranged therein for aspirating the fluids from the wound bed (W), and a fluid collection container for collecting the aspirated fluids. Moreover, the appliance has a first measuring device and a second measuring device. The first measuring device serves to determine the quantity of the aspirated fluids, and the second
(Continued)

measuring device serves to determine the quantity of the substance delivered to the body.

12 Claims, 4 Drawing Sheets

(52) U.S. Cl.
CPC ......... *A61M 3/022* (2014.02); *A61M 2205/15* (2013.01); *A61M 2205/3317* (2013.01); *A61M 2205/3389* (2013.01); *A61M 2205/3393* (2013.01)

(58) Field of Classification Search
CPC ...... A61M 2205/15; A61M 2205/3317; A61M 2205/3389; A61M 2205/3393
USPC .......................................................... 604/543
See application file for complete search history.

(56) References Cited

U.S. PATENT DOCUMENTS

| | | |
|---|---|---|
| 2013/0211318 A1 | 8/2013 | Croizat et al. |
| 2015/0105718 A1* | 4/2015 | Hutchinson ........... A61F 13/148 604/43 |
| 2016/0045648 A1 | 2/2016 | Locke et al. |
| 2016/0325028 A1* | 11/2016 | Locke ............... A61F 13/00068 |

FOREIGN PATENT DOCUMENTS

| | | | |
|---|---|---|---|
| EP | 1 977 776 A2 | 10/2008 | |
| EP | 2 480 263 B1 | 9/2016 | |
| WO | WO-0007653 A1 * | 2/2000 | .......... A61M 1/0027 |
| WO | WO-2005/105180 A1 | 11/2005 | |
| WO | WO-2008/043067 A2 | 4/2008 | |
| WO | WO-2008043067 A2 * | 4/2008 | .......... A61M 1/0058 |
| WO | WO-2009141820 A1 * | 11/2009 | .......... A61M 1/0031 |
| WO | WO-2010/033272 A1 | 3/2010 | |
| WO | WO-2015/086857 A1 | 6/2015 | |
| WO | WO-2015/094724 A1 | 6/2015 | |

OTHER PUBLICATIONS

Bobkiewicz, Adam et al.; Negative pressure wound therapy with instillation (NPWTi): Current status, recommendations and perspectives in the context of modern wound therapy; Negative Pressure Wound Therapy Journal, [S.I.], v. 3, n. 1, Apr. 2016.

Gupta, Subhas et al.; Clinical recommendations and practical guide for negative pressure wound therapy with instillation; Int Wound J, Apr. 2016;13(2): 159-174.

* cited by examiner

APPLIANCE AND METHOD FOR WOUND THERAPY BY MEANS OF NEGATIVE PRESSURE AND DELIVERY OF A SUBSTANCE

CROSS-REFERENCE TO RELATED APPLICATION

This present application is the US national phase of International Patent Application No. PCT/EP2018/050275, filed Jan. 5, 2018, which claims priority to European Application No. 17150814.6, filed Jan. 10, 2017. The priority application, EP 17150814.6, is hereby incorporated by reference in its entirety.

TECHNICAL FIELD

The present invention relates to an appliance for negative-pressure therapy of wounds in which, on the one hand, a substance is delivered to a wound bed and, on the other hand, fluids, in particular an exudate and the delivered substance, are aspirated from the wound bed by means of negative pressure. Appliances of this kind are used in the medical sector, particularly in negative-pressure wound therapy combined with instillation or irrigation. The invention further relates to a corresponding method for negative-pressure wound therapy on the human or animal body.

PRIOR ART

It has long been known in the medical field that wound healing, particularly in the case of large and/or poorly healing wounds, can be improved by means of negative-pressure wound therapy (NPWT) of the wound bed. Body fluids or secretions are aspirated from the wound bed by means of a pump. During the negative-pressure therapy, the wound healing can additionally be influenced in a positive way by delivering a substance to the wound bed. Methods of this kind are known as negative-pressure wound therapy with combined instillation or irrigation. Depending on the type and size of the wound, the aspiration and the delivery take place simultaneously, in succession and/or in intermittent alternation.

The substance to be delivered can be, for example, a physiological or non-physiological saline solution, a pharmaceutical or a mixture thereof. The substance can be used, for example, to promote wound healing, to prevent infections, to provide local anaesthesia or to improve blood clotting by inhibition of fibrinolysis. The delivery of the substance can thus serve for irrigation or for therapeutic, diagnostic and/or preventive purposes.

General descriptions of wound therapy by combined negative-pressure therapy and instillation are found, for example, in the publication by Bobkiewicz, Adam et al.: Negative pressure wound therapy with instillation (NPWTi): Current status, recommendations and perspectives in the context of modern wound therapy; Negative Pressure Wound Therapy Journal, [S.1.], v. 3, no. 1, April 2016; or in the publication by Gupta, Subhas et al.: Clinical recommendations and practical guide for negative pressure wound therapy with instillation; Int Wound J, 2016 Apr. 13(2): 159-174.

As in conventional infusion, the substance to be delivered is often delivered by means of a bag or bottle of liquid filled with the substance being held high over the body area to be treated, such that the substance is delivered by hydrostatic pressure through a delivery line to the site to be treated. Separately from this, the body fluids are aspirated by a vacuum pump via a corresponding line.

To permit better adjustment and regulation when delivering the substance and/or to be independent of the arrangement and in particular the height position of the liquid container filled with the substance, systems have also long been known in which the substance is delivered to the body by means of a pump, in particular a so-called peristaltic or hose pump.

To monitor the therapy, many systems of the prior art involve measuring the pressure in the wound area either continuously or at regular time intervals. This is achieved, for example, by means of an auxiliary line which opens laterally into the secretion line in the area of the patient-side end of the secretion line or which is routed separately from the secretion line through the wound cover and opens directly into the wound area.

DE 10 2013 226 708 A1 discloses a system for wound therapy by combined negative-pressure therapy and instillation, with a negative-pressure unit and, provided separately from the latter, an instillation unit. By means of wireless communication it is ensured that the operations of the negative-pressure unit and of the instillation unit are adapted to each other.

WO 2015/094724 discloses an appliance in which the pressure in the wound area is monitored in order to regulate the delivery of the instillation liquid on the basis of the monitoring.

Further wound therapy appliances in which aspiration of fluid is combined with instillation or irrigation, and in which pressure is monitored, are disclosed in the documents WO 2005/105180 A1, EP 1 977 776 A2 and US 2013/0211318 A1.

EP 0 865 304 B1 and US 2016/0045648 A1 each disclose appliances for negative-pressure wound therapy in which, by measuring pressure in the suction line, it is possible to establish whether the fluid collection container is full or not. In the wound therapy appliance disclosed in EP 2 480 263 B 1, monitoring of pressure in the suction line serves to establish deviations from the normal course of therapy in order, if appropriate, to trigger an alarm.

Moreover, a number of prior art documents are cited below which relate, however, to medical fields other than negative-pressure wound therapy combined with instillation or irrigation.

WO 2015/086857 A1 discloses a system for flushing a pericardial cavity, in which system the flushing procedure is regulated on the basis of the flow rates, measured by sensors, of the delivered and removed liquids in conjunction with the haematocrit value and a pressure measurement in the wound space.

US 2010/0259283 A1 proposes determining the filling level in a container of an implantable medication delivery appliance by measuring the electrical resistance.

WO 2010/033272 A1 discloses an appliance which, in a medical emergency, is used for rapid aspiration of internal accumulations of liquid. At the same time, a liquid is delivered for irrigation purposes. The quantities of the liquids delivered and aspirated are measured and evaluated.

SUMMARY OF THE INVENTION

It is an object of the present invention to make available an appliance for negative-pressure wound therapy combined with instillation or irrigation, by means of which appliance the procedures taking place during the therapy can be better monitored and, in particular, can be controlled.

In order to achieve this object, the present invention makes available an appliance for healing wound tissue by means of negative-pressure therapy of wounds on the human or animal body in which, on the one hand, a substance is delivered to a wound bed and, on the other hand, fluids, in particular an exudate and the delivered substance, are aspirated from the wound bed by means of negative pressure. The appliance has a suction pump housing, with a suction pump arranged therein for aspirating the fluids from the wound bed, and a fluid collection container for collecting the aspirated fluids. The appliance moreover has a first measuring device for determining the quantity of the aspirated fluids, and a second measuring device for determining the quantity of the substance delivered to the body.

The appliance is thus designed for negative-pressure therapy of wounds with combined instillation or irrigation. During the therapy, therefore, a substance is delivered to the wound bed. At the same time or in a staggered manner, fluids are aspirated from the wound area by means of the suction pump. The fluids that are aspirated can be, in particular, body fluids such as exudate which forms in the wound bed. However, the fluids can also include at least some of the substance delivered to the wound bed.

The expressions "quantity of the aspirated fluids" and "quantity of the substance delivered to the body" designate in particular the current volumetric flows, or the volumetric flows averaged over a period of time, of the fluids or of the substance. However, they also cover in particular the weight or the volume of the fluids aspirated by a defined point in time or of the substance delivered by a defined point in time. By means of the first and the second measuring device, a physical parameter is thus measured that is directly in relation to the volume or weight of the aspirated fluids or of the delivered substance.

Whereas many appliances of this kind in the prior art determine the pressure in the wound area in order to monitor and control the negative-pressure therapy, this purpose is served, according to the invention, by determining the quantity of aspirated fluid and the quantity of the delivered substance. An additional pressure measurement can of course be carried out in particular in the wound area in order to further optimize the monitoring and control. By measuring the quantities of fluid and of substance, it is possible in particular to precisely determine the quantity of the substance absorbed by the body and/or the exudate secreted from the body in the wound area. For example, it is possible to ensure that the delivered substance does not remain in the body, which is important particularly with respect to irrigation if a fluid substance is delivered to the body over quite a long period of time. However, the determination of the quantities of fluid and of substance can also simply serve to prevent an overpressure in the wound area. The detection of bleeding, which poses a major problem in negative-pressure wound therapy, is a further and very advantageous possibility. In any case, the determination of the quantities of fluid and of substance by the first and the second measuring device allows a direct conclusion to be drawn concerning the parameters that are in fact decisive for the therapy, thus permitting improved monitoring and control of the therapy procedure.

The negative-pressure therapy according to the invention usually entails a procedure that lasts for several hours and that may even last for several days or weeks. Generally speaking, the duration of the negative-pressure therapy is such that it gives the wound tissue at least the chance to heal, or it lasts at least until a healing process induced by the therapy is established or, if appropriate, can be excluded. Generally speaking, the healing process is marked in particular by a change of the wound tissue.

The substance delivered to the wound bed can be, for example, a physiological or non-physiological saline solution, a pharmaceutical or a mixture thereof. The instillation substance can also serve to flush the wound bed. However, it can also serve to introduce a medicament or to provide local anaesthesia of the wound area. The instillation substance can in this case optionally be preconditioned, for example, with a defined temperature, UV radiation, and/or a defined chemical composition or mixture.

The appliance can in particular also have a substance container, from which the substance to be delivered is made available. The substance container can be produced from a flexible material or a rigid material. However, it is advantageously produced from a transparent material, such that the filling level can be seen clearly from the outside.

The suction pump is preferably a vacuum pump, in particular a diaphragm pump. A diaphragm pump generally has at least one diaphragm and a pump chamber delimited by the diaphragm. When using a diaphragm pump, an oscillating pressure profile generally arises in the wound area on account of the periodic pump movements. An oscillating pressure profile of this kind can have a positive effect on the healing of the wound. Of course, precautionary measures may be taken to avoid the oscillating pressure profile caused in the wound area by the pump movements, such that the negative pressure on the wound bed is in each case largely compensated, i.e. averaged, during a cycle of the diaphragm pump. The pump chamber is advantageously arranged completely in the interior of the suction pump housing.

The appliance is preferably designed for the intermittent aspiration of the fluids, that is to say the aspiration procedure has pauses during which no fluid is aspirated. It has been found that intermittent aspiration can have a positive effect on the healing of the wound. The time intervals during which the aspiration takes place are preferably many times longer than the time intervals during which no aspiration takes place. Depending on the size and nature of the wound, the aspiration intervals advantageously last from one to six hours, and the intervals during which no aspiration takes place preferably last from one to thirty minutes. The choice of the intervals in these ranges leads to particularly rapid wound healing. The aspiration cycle, with aspiration interval and interval without aspiration, is generally repeated several times, that is to say at least twice, but advantageously at least three times, and particularly advantageously at least five times.

In addition to the intermittent aspiration, or as an alternative thereto, the appliance is preferably designed for intermittent delivery of the substance to the wound area. An appliance designed both for intermittent aspiration and for intermittent substance delivery is particularly advantageous for the healing of the wound. The intermittent aspiration then preferably has a periodicity which is coordinated with the periodicity of the intermittent delivery of the substance. In order to permit an optimal effect of the delivered substance on the wound tissue, the appliance is preferably designed to deliver the substance in each case directly before a pause in the aspiration and then, during a time interval of advantageously 1 to 30 minutes, not only to break off the aspiration but also the substance delivery.

The appliance can have a visual or acoustic indicator by means of which the course or status of the therapy can be indicated on the basis of the quantity of the aspirated fluids determined by the first measuring device and/or on the quantity of the delivered substance determined by the second measuring device. For example, an alarm can be triggered if the fluid collection container is full, the fluid-dispensing container (instillation container) is empty, or the delivered and/or aspirated quantity is below or above certain predefined values. It is also possible that an alarm is triggered if, for example, bleeding is detected in the wound area, which may be of great importance particularly in uses in heart surgery. The indicated course or status, and in particular the alarm trigger, is preferably based on a comparison or a calculation in the sense of a mathematical link between the quantities determined by the first and the second measuring device. The mathematical link can in particular comprise a difference formation between the quantities determined by the first and the second measuring device. By determining the difference of the delivered and aspirated quantities of fluid, it is possible, for example, to detect or prevent pooling. When pooling occurs, less fluid is aspirated than fluid is delivered, as a result of which a pool of fluid, which is disadvantageous for the course of therapy, is formed in the wound area.

In a particularly preferred embodiment, the appliance moreover has a control unit which is connectable to the first measuring device and to the second measuring device and which is designed to control the suction pump. The connection of the control unit to the first and the second measuring device can be by cable or can be wireless. The connection serves to produce data communication between the control unit and the first or the second measuring device, such that the quantities determined by the first measuring device and by the second measuring device can be forwarded to the control unit.

The control unit is preferably designed to control the suction pump on the basis of the quantity of the aspirated fluids determined by the first measuring device and/or on the basis of the quantity of the delivered substance determined by the second measuring device. The control unit can perform this control, for example, on the basis of predefined limit values for the aspirated quantity of fluid and/or the delivered quantity of substance, such that, when these limit values are exceeded or not reached, the suction pump capacity is accordingly adapted by the quantities determined by the first and the second measuring device. However, the control unit is preferably designed to regulate the suction pump capacity on the basis of a comparison or a calculation in the sense of a mathematical link between the quantities determined by the first and the second measuring device. The control unit can in this case be designed in particular to determine the difference between the determined quantities of aspirated fluids and of delivered substance and to control the suction pump on the basis of this determined difference. Optimal control of the suction pump can be achieved in this way.

The control unit is in this case advantageously designed to control the suction pump in such a way that it increases the suction capacity of the suction pump if the quantity of the delivered substance is greater than the quantity of the aspirated fluids. It is also advantageously designed to gradually reduce the suction capacity of the suction pump when the quantity of the aspirated fluids, and in particular of the exudate, becomes smaller over the course of the negative-pressure therapy.

The control unit is advantageously arranged inside or on the suction pump housing. The second measuring device can likewise be arranged inside or on the suction pump housing. In this case, for example, provision can be made that a delivery line for delivering the substance to the wound area runs at least partially on or in the suction pump housing, such that the quantity of substance conveyed through this delivery line can accordingly be determined by the second measuring device.

In a preferred embodiment, however, the second measuring device is arranged at a distance from the suction pump housing. In this embodiment in particular, a wireless connection between the second measuring device and a control unit arranged in or on the suction pump housing is advantageous.

The second measuring device can be arranged in the area of an instillation container, which contains the substance to be delivered, and it can be designed to measure the filling level in the instillation container. However, it can also be designed to be arranged inside a delivery line which serves to deliver the substance to the human or animal body. In such an embodiment, the determination of the delivered quantity by the second measuring device is generally based on a determination of the flowrate.

To determine the quantity of the delivered substance, the second measuring device preferably has a drop counter, a weight sensor, a capacitive filling level sensor or a flow meter.

In a specific embodiment, the suction pump housing has a holder for holding a container with the substance to be delivered. The second measuring device then preferably has a weight sensor mounted on the suction pump housing for the purpose of determining the weight bearing on the holder. The quantity of the delivered substance can be determined very easily in this way.

The substance to be delivered can be contained in a liquid bag or in a bottle arranged at a height above the wound area, such that the substance is delivered through a delivery line to the wound area on account of the hydrostatic pressure. Particularly when the substance is delivered in this way, the second measuring device can have a drop counter which is designed for arrangement inside the delivery line. Such an appliance is particularly easy to set up if the second measuring device additionally has a transmitting unit for wireless communication with a control unit arranged in or on the suction pump housing.

In specific embodiments, the appliance can have a peristaltic pump arranged in or on the suction pump housing and serving to deliver the substance to the human or animal body.

That is to say, the substance is then delivered to the wound bed by means of the peristaltic pump. This permits better adjustment and regulation during delivery of the substance. Moreover, one is then independent of the arrangement, in particular the height, of the liquid container filled with the substance.

Particularly in the embodiments with a peristaltic pump arranged in or on the suction pump housing or with a peristaltic pump arranged in or on the fluid collection container or with at least one head of a peristaltic pump arranged in or on the fluid collection container, but also in other embodiments, a control unit can be provided which is designed to control the delivery of the substance to the wound bed on the basis of the quantity of fluid determined by the first measuring device and/or on the basis of the quantity of the delivered substance determined by the second measuring device. The control unit can perform this control, for example, on the basis of predefined limit values for the aspirated quantity of fluid and/or the delivered quantity of substance, such that, when these limit values are exceeded or not reached, the delivery of the substance to the wound bed is accordingly adapted by the quantities determined by the first and the second measuring device. However, the control unit is preferably designed to regulate the substance delivery on the basis of a comparison or a calculation in the sense of a mathematical link between the quantities determined by the first and the second measuring device. The control unit can in this case be designed in particular to determine the difference between the determined quantities of aspirated fluids and of delivered substance and to control the suction pump on the basis of this determined difference. Optimal control of the substance delivery can be achieved in this way. Particularly if the control unit is also designed to control the fluid aspiration on the basis of the quantity of fluid determined by the first measuring device and/or on the basis of the quantity of the delivered substance determined by the second measuring device, it is possible to achieve optimal and automated regulation of the wound therapy.

If a peristaltic pump is provided which is arranged in or on the suction pump housing or in or on the fluid collection container, or if the head of a peristaltic pump is arranged on the fluid collection container and for example is driven by a motor arranged in the suction pump housing, then the second measuring device can be designed to determine the quantity of the delivered substance on the basis of the suction pump capacity and/or on the basis of the pump energy that is output by the peristaltic pump during a certain period of time.

A particularly simple embodiment is one in which the first measuring device is designed to determine the quantity of the fluids collected in the fluid collection container and for this purpose has a capacitive filling level sensor or a weight sensor.

The aforementioned control unit, connectable to the first measuring device and to the second measuring device, can additionally or alternatively be designed to control the substance delivery on the basis of the quantity of the aspirated fluids determined by the first measuring device and/or on the basis of the quantity of the delivered substance determined by the second measuring device. For this purpose, the control unit can be designed, for example to regulate the flowrate through a pinch valve or to regulate the discharge capacity of a peristaltic pump. The control unit can in this case be connected to the pinch valve or to the peristaltic pump by a cable connection or by a wireless connection. The regulation is preferably based on a difference, determined by the control unit, between the quantity of the aspirated fluids and the quantity of the delivered substance.

The invention moreover relates to a method for healing wound tissue by means of negative-pressure therapy of wounds on the human or animal body. In this method, which is preferably but not necessarily carried out using the abovementioned appliance, a substance is, on the one hand, delivered to a wound bed and, on the other hand, fluids, in particular an exudate and the delivered substance, are aspirated from the wound bed by means of negative pressure. The method has at least the following method steps:

aspirating the fluids from the wound bed by means of a suction pump;
delivering the substance to the wound bed;
determining the quantity of the aspirated fluids;
determining the quantity of the delivered substance;
comparing the quantity of the aspirated fluids with the quantity of the delivered substance, in particular by difference calculation.

The abovementioned method steps can be carried out in any desired sequence.

The method preferably also comprises the step by which the aspiration of the fluids and/or the delivery of the substance is regulated on the basis of the comparison, in particular the difference, between the quantity of the aspirated fluids and the quantity of the delivered substance.

BRIEF DESCRIPTION OF THE DRAWINGS

Preferred embodiments of the invention are described below with reference to the drawings, which are provided only for explanatory purposes and are not to be interpreted as limiting the invention. In the drawings.

DESCRIPTION OF PREFERRED EMBODIMENTS

FIGS. 1 to 6 show various embodiments of appliances according to the invention for the negative-pressure therapy of wounds on the human or animal body.

Elements having an identical or similar technical function and effect are in each case provided with the same reference signs in the various embodiments in FIGS. 1 to 6.

The appliances shown in FIGS. 1 to 6 each have a suction pump housing 2 with a suction pump (not shown in the figures) arranged therein for aspirating fluids from a wound bed W of a patient P. The wound bed W is covered by means of a wound cover 1. The wound cover 1 closes off the area of the wound bed W from the outside in a manner that is as airtight as possible.

In all of the embodiments shown in FIGS. 1 to 6, a fluid collection container 3 is mounted on the suction pump housing 2, although in principle it could also be arranged at a distance from the suction pump housing 2 and connected to the latter via a connection line. The fluid collection container 3 serves to collect the fluids aspirated from the wound bed W by the suction pump.

Figure 1:
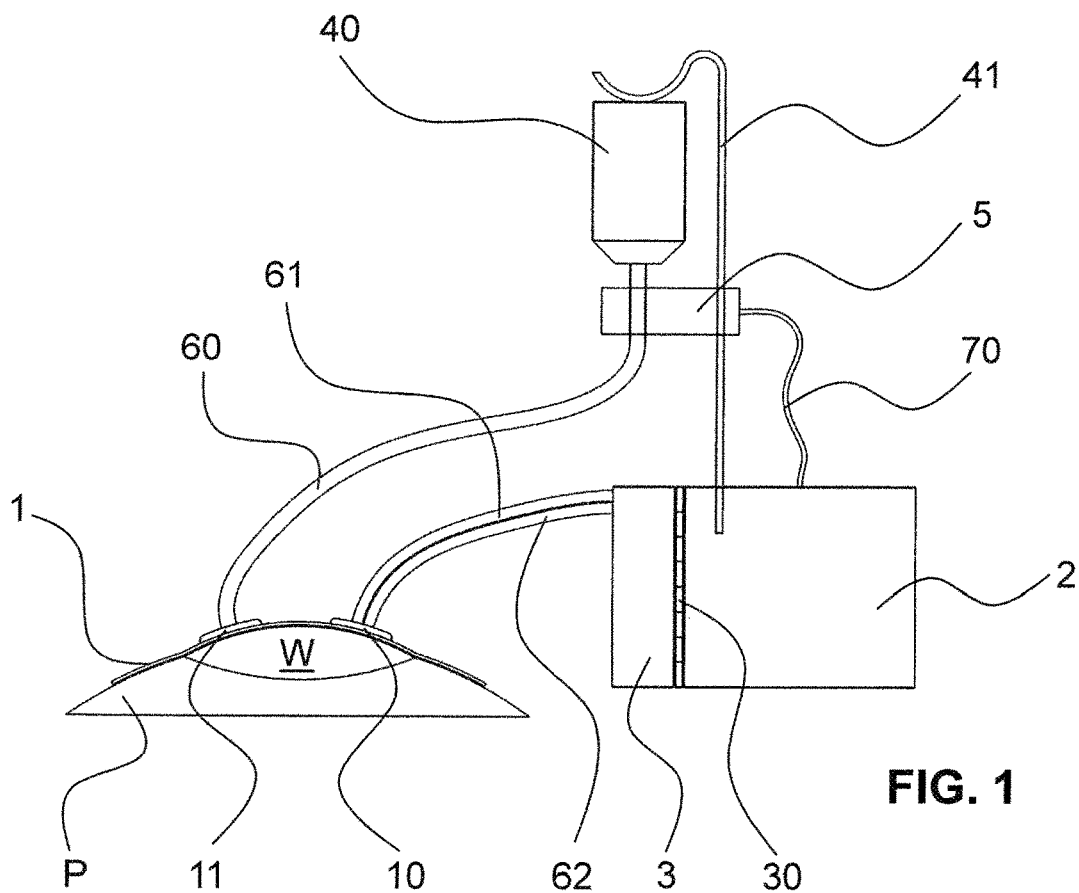
FIG. 1 shows a schematic view of an appliance according to the invention in a first embodiment.

As can be seen from the first embodiment shown in FIG. 1, for example, the fluids are aspirated from the wound bed W via a secretion line 61. By way of a first, patient-side line end, the secretion line 61 is in fluidic communication with the area of the wound bed W located underneath the wound cover 1. As is shown in FIG. 1, the secretion line 61 can for this purpose, for example, be attached to a drainage port 10 arranged on the wound cover 1. The drainage port 10 establishes the connection between the wound area and the secretion line 61 and makes it easier to attach and remove the secretion line 61 to and from the wound cover 1. By way of a second line end on the side of the suction pump housing, the secretion line 61 opens into the interior of the fluid collection container 3.

During operation, the suction pump generates a negative pressure in the fluid collection container 3, i.e. a pressure below atmospheric pressure, in order to aspirate fluids from the wound bed W via the secretion line 61 and to collect them in the fluid collection container 3. For this purpose, the suction pump, which can in particular be a diaphragm pump, is connectable to the interior of the fluid collection container 3 via a line that is not shown in the figures. The air aspirated by the suction pump is expelled into the environment via an outlet that is not shown in the figures.

Parallel to the secretion line 61, an auxiliary line 62 leads from the wound bed W to the pump assembly housing 2 via the fluid collection container 3. By means of the auxiliary line 62, it is possible, if necessary, to flush the secretion line 61 and/or to measure the pressure in the secretion line 61. For this purpose, the auxiliary line 62 opens into the secretion line 61 preferably in proximity to the wound bed W, although, as is shown in FIG. 1, it can also open directly into the wound bed W via the drainage port 10.

In order to deliver a substance, for example a physiological or non-physiological saline solution, a pharmaceutical, an anaesthetic or a mixture thereof, to the wound bed W, an instillation line 60 is provided which opens with a first end into the wound bed W and is connected with a second end to the interior of an instillation bag 40. As is shown in FIG. 1, the instillation line 60 can be attached to an instillation port 11 arranged on the wound cover 1 and can open into the wound bed W via this instillation port 11. The instillation port 11 can in particular make it easier to attach and remove the instillation line 60 to and from the wound cover 1.

The instillation bag 40 contains an instillation liquid, which is the substance to be delivered to the wound bed W during the negative-pressure therapy. The instillation bag 40 is suspended via a hanger on a suspension bracket 41. To exploit the hydrostatic pressure when delivering the instillation liquid, the instillation bag 40 is in this case arranged above the wound bed W with respect to the direction of gravity. In the embodiment shown in FIG. 1, the suspension bracket 41 is held in the suction pump housing 2. The quantity of instillation liquid delivered to the wound bed W can be regulated, for example, by means of a simple pinch valve 50 which is arranged in the instillation line 60 underneath the instillation bag 40 or in, for example, the drop counter unit with the drop counter 5 (see FIG. 2).

In the first embodiment according to FIG. 1, the quantity of the fluids aspirated from the wound bed is determined by means of a capacitive filling level sensor 30. The filling level in the fluid collection container 3 is measured by means of the capacitive filling level sensor 30. The capacitive filling level sensor 30, which thus forms a measuring device, is for this purpose mounted on the inner face or outer face of the fluid collection container 3. The filling level sensor 30 is connected to a control unit (not visible in FIG. 1) arranged in the suction pump housing 2, such that the filling level values measured by the filling level sensor 30 can be transmitted to the control unit and can be retrieved from the latter.

A further measuring device in the form of a drop counter 5 is arranged under the instillation bag 40 inside the instillation line 60. The drop counter 5, of which the possible configurations are well known to a person skilled in the art, serves for measuring the flow rate of the instillation liquid in the instillation line 60. The drop counter 5 is in this case mounted on the suspension bracket 41 and, via a cable connection 70, is connected to the control unit arranged in the suction pump housing 2. The measured values determined by the drop counter 5 can be transmitted to the control unit or retrieved therefrom via the cable connection 70.

By means of the control unit, the fluid quantities that have been measured by the drop counter 5 and by the capacitive filling level sensor 30 can now be presented, for example, on a display (not shown in FIG. 1). In this way, the specialist medical personnel and/or the patients can at any time apprise themselves of the current status of the negative-pressure therapy and, if appropriate, for example, can completely discontinue or interrupt the therapy or readjust the delivery of the instillation liquid and/or adapt the suction capacity of the suction pump.

However, the fluid quantities measured by the drop counter 5 and by the capacitive filling level sensor 30 are preferably processed further in the control unit, for example by being compared with predefined limit values. On the basis of this further processing, the control unit can, for example, cause an alarm to be triggered and/or cause the suction capacity of the suction pump to be regulated. In the further processing, a difference between the quantity of aspirated fluids and the quantity of the delivered instillation liquid is preferably formed by the control unit. It is thereby possible to determine or at least estimate the quantity of instillation liquid received by the body of the patient P and/or the quantity of the exudate secreted from the wound bed W. This permits very direct and meaningful monitoring of the course of therapy. It is thereby also possible to detect any leakage or any loss of sealing in the area of the wound cover 1 (escape of liquid).

Figure 2:
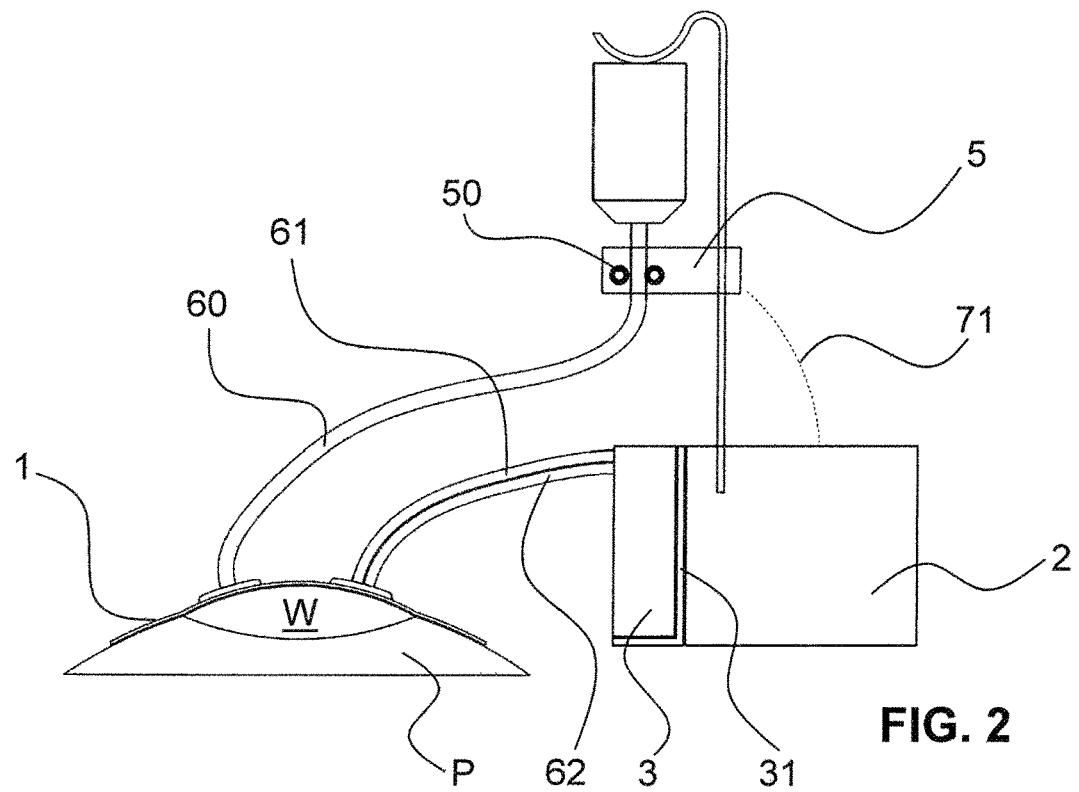
FIG. 2 shows a schematic view of an appliance according to the invention in a second embodiment.

The second embodiment, shown in FIG. 2, differs from the first embodiment of FIG. 1 in that, on the one hand, the filling level in the fluid collection container 3 is determined by means of a weight sensor 31, and, on the other hand, the connection between the drop counter 5 and the control unit arranged in the suction pump housing 2 is a wireless connection 71. The weight sensor 31 can be mounted on the fluid collection container 3 or on the suction pump housing 2.

Figure 3:
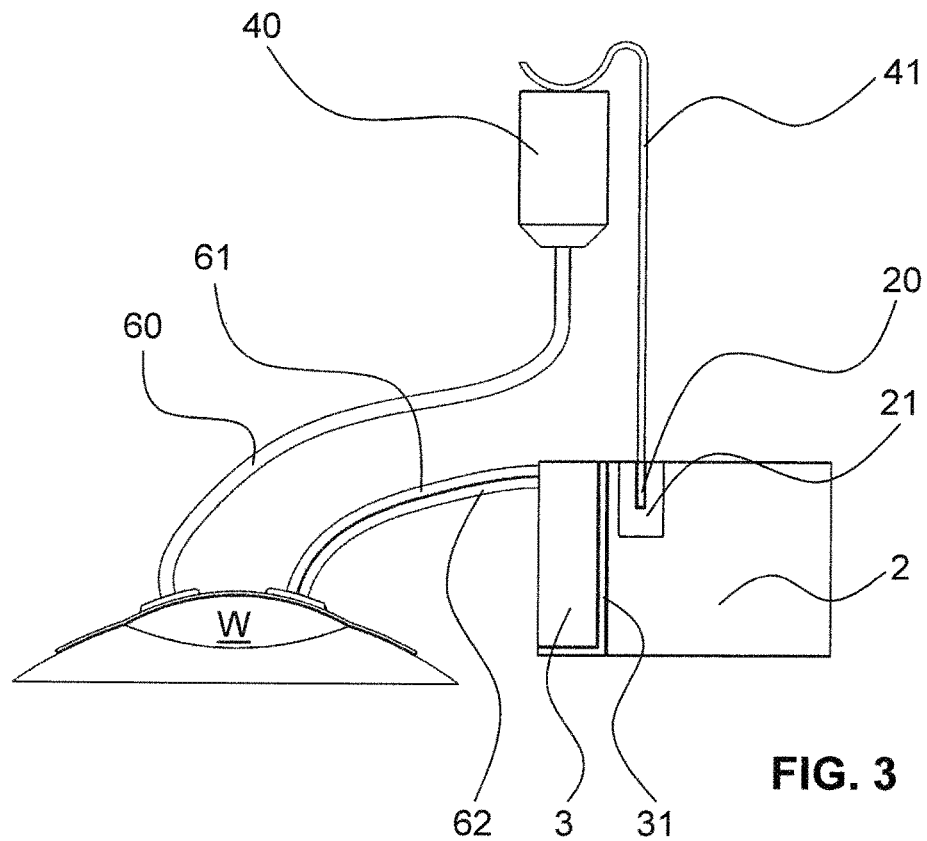
FIG. 3 shows a schematic view of an appliance according to the invention in a third embodiment.

The third embodiment, shown in FIG. 3, differs from the second embodiment of FIG. 2 in that the quantity of the instillation liquid delivered to the wound bed W is determined by means of a weight sensor 21. The suspension bracket 41 is for this purpose held with its lower end in a holder 20 provided on the suction pump housing 2. The weight loading the holder 20 is measured by means of the weight sensor 21 and, when a change of weight is detected, a conclusion can be drawn regarding the quantity of the instillation liquid delivered to the wound bed W. This embodiment is particularly advantageous since the whole appliance is especially easy for the user to set up prior to the therapy.

Figure 4:
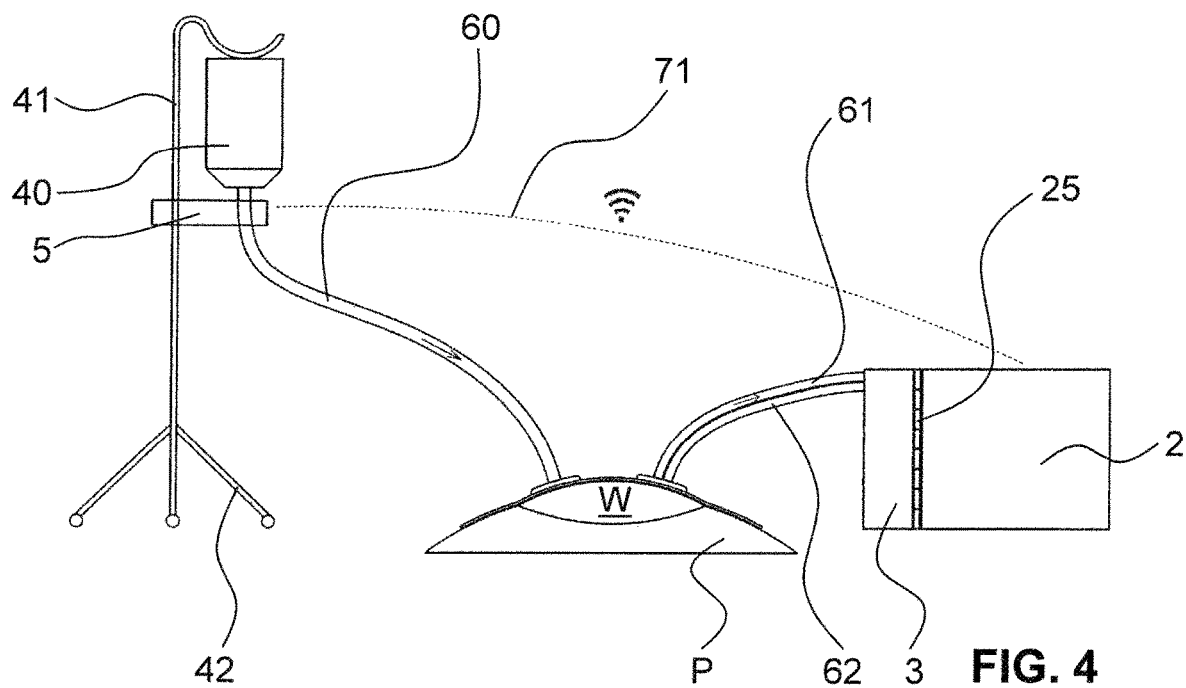
FIG. 4 shows a schematic view of an appliance according to the invention in a fourth embodiment.

The fourth embodiment, shown in FIG. 4, differs from the first embodiment of FIG. 1 in that a capacitive filling level sensor 25 is provided for measuring the filling level in the fluid collection container 3 and is mounted on the suction pump housing 2, and in that the suspension bracket 41 has a stand 42 in order to allow the suspension bracket 41 including the instillation bag 40 to be placed at a distance from the suction pump housing 2. Moreover, the values measured by the drop counter 5 are transmitted to the control unit arranged in the suction pump housing 2 via a wireless connection 71. The arrangement of the filling level sensor 25 on the suction pump housing 2 has the advantage that the fluid collection container 3, which is usually frequently replaced and disposed of together with the contents, is easier to produce. The embodiment in FIG. 4 shows in particular that the appliance according to the invention can be readily combined with a conventional device for delivering the instillation liquid. The drop counter 5 simply has to be arranged inside the instillation line 60. On account of the wireless data transmission via the wireless connection 71, no additional cable connections are needed.

Figure 5:
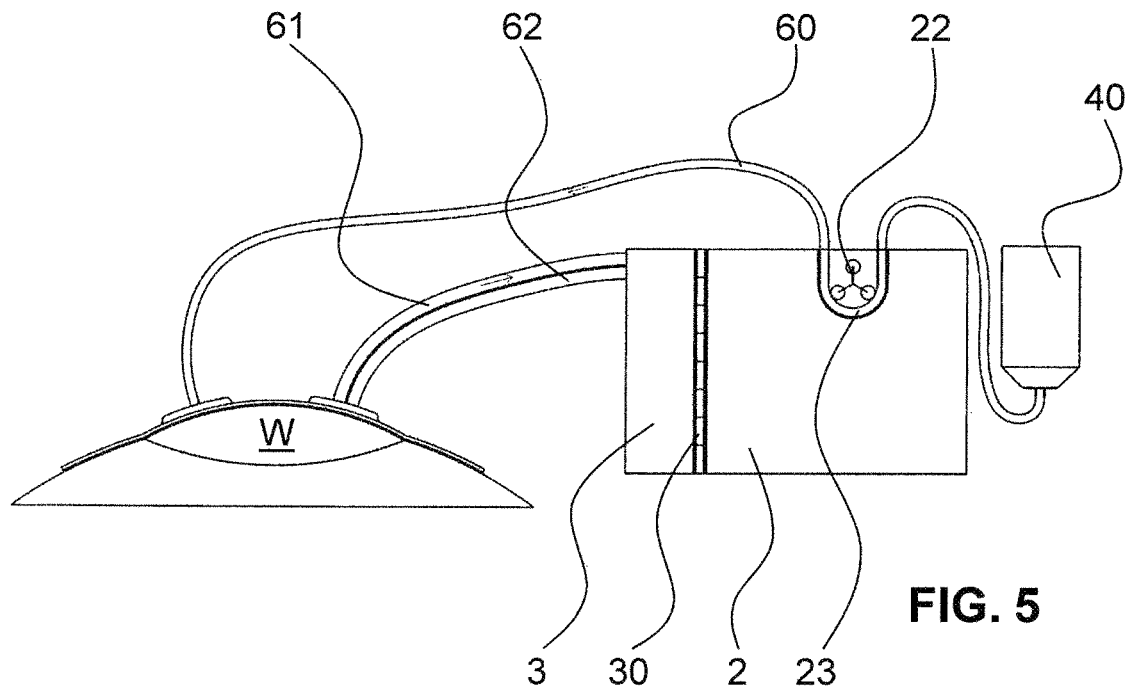
FIG. 5 shows a schematic view of an appliance according to the invention in a fifth embodiment.

The fifth embodiment, shown in FIG. 5, differs from the first embodiment of FIG. 1 in particular in that a peristaltic pump 22 is arranged on the suction pump housing 2 in order to convey the instillation liquid present in the instillation line 60 to the wound bed W. The instillation line 60 is for this purpose placed on a hose guide 23 provided on the suction pump housing 2 in the area of the peristaltic pump 22. In this embodiment, the instillation bag 40 does not necessarily have to be arranged above the wound bed W. Moreover, by adjusting the discharge capacity of the peristaltic pump 22, it is possible to achieve very simple and, in particular, automated regulation of the delivery of the instillation liquid. The quantity of instillation liquid delivered through the instillation line 60 can be easily determined, for example, by using the respective discharge capacity of the peristaltic pump 22.

Figure 6:
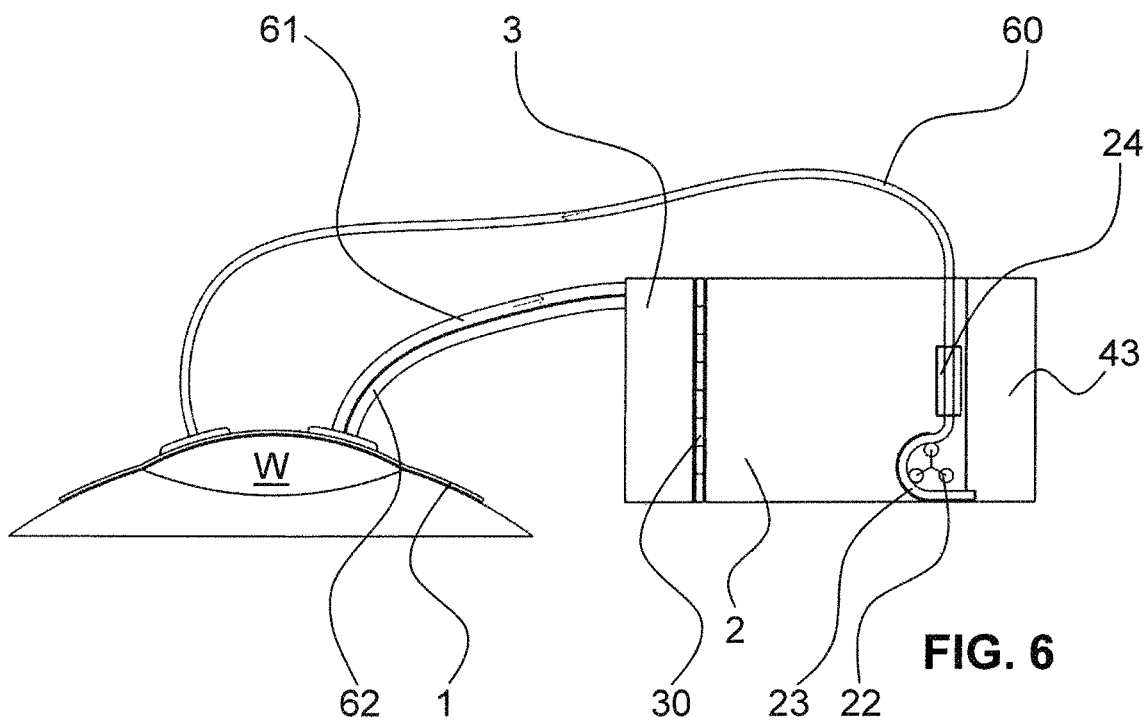
FIG. 6 shows a schematic view of an appliance according to the invention in a sixth embodiment.

The sixth embodiment, shown in FIG. 6, differs from the fifth embodiment of FIG. 5 in that the instillation container, in which the instillation liquid to be delivered is contained, is mounted in the form of an instillation canister 43 directly on the suction pump housing 2 just like the fluid collection container 3. Here, the quantity of the instillation liquid delivered through the instillation line 60 is determined by a flow meter 24 arranged in or on the suction pump housing 2.

Figure 7:
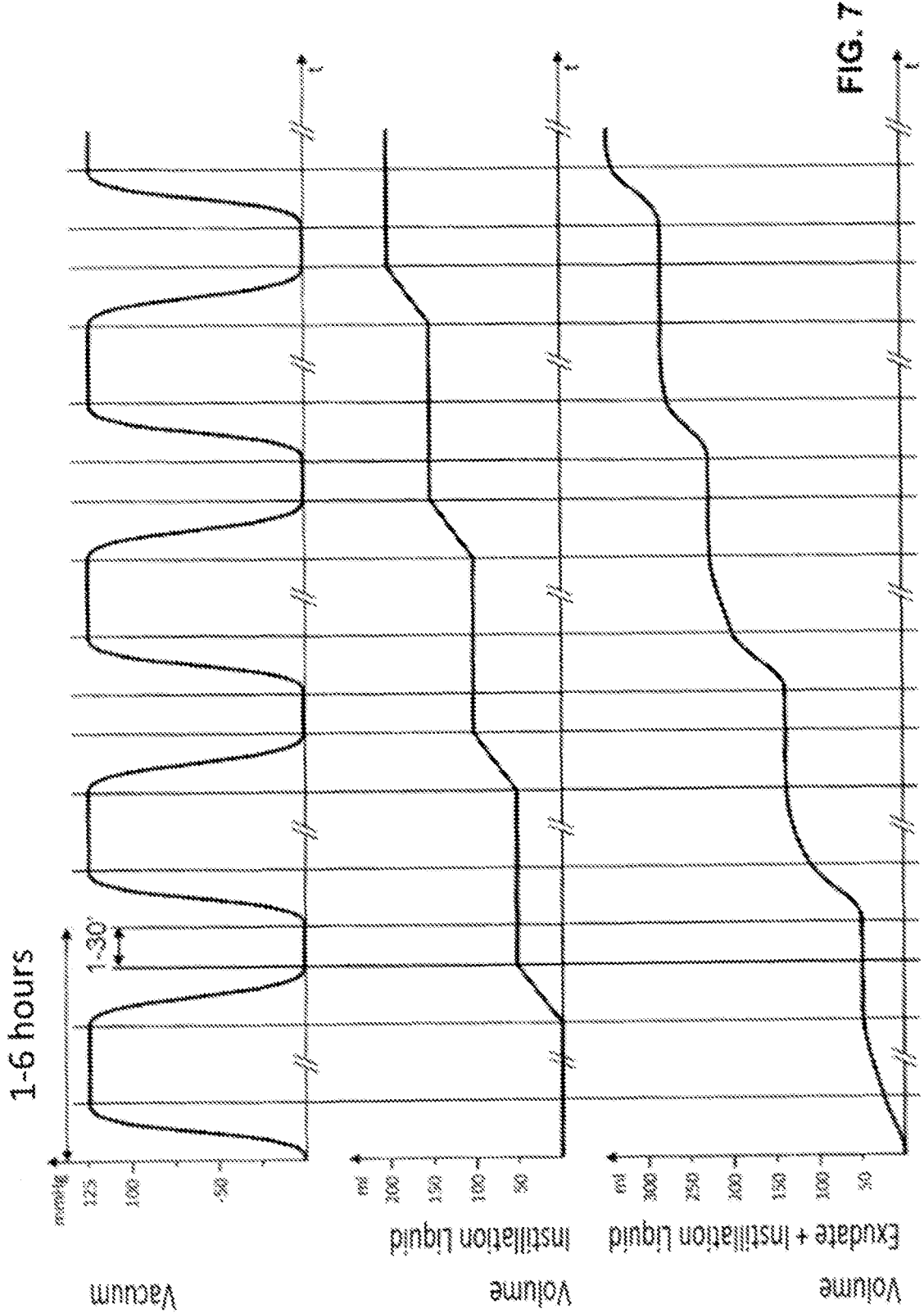
FIG. 7 shows a typical example of the curve profiles present during the operation of an appliance according to the invention for the negative pressure, the delivered quantity of instillation liquid, and the quantity of the aspirated fluids.

FIG. 7 shows typical curve profiles that are obtained, when using an appliance according to the invention or the method according to the invention, for the negative pressure prevailing in the wound bed W (top graph), for the volume of instillation liquid delivered (middle graph), and for the volume of the fluids aspirated from the wound bed W (bottom graph). Of course, the curve profiles that actually occur during wound therapy depend in particular on the size and nature of the wound.

The curve profiles illustrated in FIG. 7 show very clearly how the quantities of liquid determined by the first and the second measuring device (bottom two graphs), if necessary in combination with pressure measurement in the area of the wound bed W for example via the auxiliary line 62 (top graph), reproduce the course of therapy and the healing process very directly.

As will be seen from the top graph in FIG. 7, a typical course of therapy lasts for several hours, if not days, so that the wound tissue is given the chance to change, in particular to heal. The aspiration of the fluids from the wound bed W in this case takes place intermittently. An aspiration procedure lasting 1 to 6 hours is followed by a rest phase, without negative pressure, lasting from one to thirty minutes. Each rest phase is preceded by a downward phase, during which the negative pressure is steadily reduced. Each rest phase is followed by an upward phase, during which the negative pressure is steadily increased again from atmospheric pressure back to a constant negative pressure. The upward and downward phases are each many times shorter than the respective aspiration phase, lying between them, at constant negative pressure.

The curve profile illustrated in the top graph of FIG. 7 would in fact be superposed by an oscillating curve profile in the negative mmHg range with a relatively short periodicity of a few seconds on account of the pump movements of the suction pump (diaphragm pump). For representational reasons, this rapidly oscillating curve profile is not shown. The illustrated curve profile reflects the respective amplitude.

As will be seen from the middle graph in FIG. 7, the instillation liquid is delivered to the wound bed W only during certain delivery phases, which are relatively short in relation to the overall duration of the therapy and which are distributed at regular time intervals across the entire duration of the therapy. The delivery phases each take place together with the downward phases of the aspiration. This ensures that aspiration still takes place, albeit at a reduced level, during the delivery of the instillation liquid, such that no overpressure can arise in the wound bed W. During the succeeding rest phase, the substance delivered to the wound bed is able to act optimally on the wound tissue.

Finally, it will be seen from the bottom graph of FIG. 7 that the volume of the fluids aspirated from the wound bed W increases sharply after each rest phase. Towards the end of the longer phases with constant negative pressure, the quantity of the aspirated fluids decreases sharply in each case, the reduction taking place more quickly with each therapy cycle on account of the healing process and on account of the resulting reduced quantity of secreted exudate. Towards the end of the therapy, it is basically only the previously delivered instillation liquid that is aspirated from the wound bed W.

Of course, the invention described here is not limited to the embodiments mentioned, and many modifications are possible. Thus, the respective features of the embodiments shown in FIGS. 1 to 6 can be combined in particular in any desired manner. The curve profiles that occur during therapy may also differ from those of FIG. 7. For example, the delivery of the substance can also be uninterrupted and constant throughout the entire duration of the therapy.

The invention claimed is:

1. An appliance for healing wound tissue by means of negative-pressure therapy of wounds on a human or animal body in which a substance is delivered to a wound bed and in which fluids are aspirated from the wound bed by means of negative pressure, said appliance having:
   a suction pump housing, with a suction pump arranged therein for aspirating the fluids from the wound bed;
   a fluid collection container for collecting the aspirated fluids;
   a peristaltic pump arranged in or on the suction pump housing, or a head of a peristaltic pump which head is arranged in or on the fluid collection container, the peristaltic pump serving to deliver the substance to the human or animal body;
   a first measuring device for determining a quantity of the aspirated fluids;
   a second measuring device for determining a quantity of the substance delivered to the human or animal body on the basis of the pump energy that is output by the peristaltic pump during a certain period of time; and
   a control unit which is connectable to the first measuring device and to the second measuring device and which is configured to determine a difference between the quantity of the aspirated fluids and the quantity of the delivered substance,
   wherein the control unit is configured to control the suction pump on the basis of this determined difference,
   wherein the control unit is additionally configured to control the suction pump on the basis of at least one of the quantity of the aspirated fluids determined by the first measuring device or of the quantity of the delivered substance determined by the second measuring device, wherein the appliance is designed for intermittent aspiration of the fluids in such a way that time intervals during which the aspiration takes place are longer by a multiple than time intervals during which no aspiration takes place and that each time interval during which the aspiration takes place comprises an upward phase, during which the aspiration is steadily increased from no aspiration to a constant aspiration, and a downward phase, during which the aspiration is steadily reduced, wherein the intermittent aspiration has a periodicity that is coordinated with a periodicity of the likewise intermittent delivery of the substance having delivery phases during which the substance is delivered and non-delivery phases during which the substance is not delivered to the human or animal body, and wherein the appliance is designed such that the delivery phases each take place together with the downward phase of the aspiration.

2. The appliance according to claim 1, wherein the control unit is arranged inside or on the suction pump housing, and the second measuring device is arranged at a distance from the suction pump housing.

3. The appliance according to claim 2, wherein the second measuring device is connectable to the control unit by means of a cable connection or wireless connection.

4. The appliance according to claim 1, wherein both the control unit and also the second measuring device are arranged inside or on the suction pump housing.

5. The appliance according to claim 1, wherein the second measuring device has a drop counter, a weight sensor, a capacitive filling level sensor or a flow meter.

6. The appliance according to claim 1, wherein the suction pump housing has a holder for holding a container with the substance to be delivered, and wherein the second measuring device has a weight sensor mounted on the suction pump housing for the purpose of determining the weight bearing on the holder.

7. The appliance according to claim 1, wherein the first measuring device has one of a capacitive filling level sensor or a weight sensor for determining the quantity of the fluids collected in the fluid collection container.

8. The appliance according to claim 1, moreover having a control unit which is connectable to the first measuring device and to the second measuring device and which is configured to control the substance delivery on the basis of the quantity of the aspirated fluids determined by the first measuring device and/or on the basis of the quantity of the delivered substance determined by the second measuring device.

9. The appliance according to claim 1, wherein the aspirated fluids comprise an exudate and the delivered substance.

10. A method for healing wound tissue by means of negative-pressure therapy of wounds on a human or animal body in which a substance is delivered to a wound bed and in which fluids are aspirated from the wound bed by means of negative pressure, said method having at least the following method steps:

intermittently aspirating the fluids from the wound bed by means of a suction pump in such a way that time intervals during which the aspiration takes place are longer by a multiple than time intervals during which no aspiration takes place and that each time interval during which the aspiration takes place comprises an upward phase, during which the aspiration is steadily increased from no aspiration to a constant aspiration, and a downward phase, during which the aspiration is steadily reduced;

delivering the substance to the wound bed by means of a peristaltic pump in such a way that a periodicity of the intermittent aspiration is coordinated with a periodicity of the likewise intermittent delivery of the substance having delivery phases during which the substance is delivered and non-delivery phases during which the substance is not delivered to the human or animal body, wherein the delivery phases each take place together with the downward phase of the aspiration;

determining a quantity of the aspirated fluids;

determining a quantity of the delivered substance on the basis of the pump energy that is output by the peristaltic pump during a certain period of time;

comparing the quantity of the aspirated fluids with the quantity of the delivered substance by means of calculating the difference between the determined quantity of the aspirated fluids and the determined quantity of the delivered substance;

controlling the negative pressure on the basis of the determined difference; and controlling the negative pressure additionally on the basis of at least one of the determined quantity of the aspirated fluids or the determined quantity of the delivered substance.

11. The method according to claim 10, wherein the aspiration of the fluids and/or the delivery of the substance is regulated on the basis of the comparison between the quantity of the aspirated fluids and the quantity of the delivered substance.

12. The method according to claim 10, wherein the aspirated fluids comprise an exudate and the delivered substance.

* * * * *